(12) United States Patent
Quincy, III et al.

(10) Patent No.: US 8,187,697 B2
(45) Date of Patent: May 29, 2012

(54) COOLING PRODUCT

(75) Inventors: Roger B. Quincy, III, Cumming, GA (US); Clifford J. Ellis, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1234 days.

(21) Appl. No.: 11/799,110

(22) Filed: Apr. 30, 2007

(65) Prior Publication Data

US 2008/0268216 A1  Oct. 30, 2008

(51) Int. Cl.
*B32B 7/02* (2006.01)
*B05D 1/36* (2006.01)

(52) U.S. Cl. .................. 428/212; 428/220; 427/407.1

(58) Field of Classification Search .................. 428/212; 427/407.1
See application file for complete search history.

(56) References Cited

U.S. PATENT DOCUMENTS

| | | |
|---|---|---|
| 2,573,791 A | 11/1951 | Howells |
| 3,261,347 A | 7/1966 | Sherman |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 3,976,049 A | 8/1976 | Yamashita et al. |
| 4,100,324 A | 7/1978 | Anderson et al. |
| 4,106,477 A | 8/1978 | Feld |
| 4,340,563 A | 7/1982 | Appel et al. |
| 4,366,804 A | 1/1983 | Abe |
| 4,377,160 A | 3/1983 | Romaine |

(Continued)

FOREIGN PATENT DOCUMENTS

EP  0370600 A1  5/1989

(Continued)

OTHER PUBLICATIONS

Machine English Translation of JP_2000/300594, Tanaka Tomoji, Refrigerant Where Hydrous Gelled Resin and Another Latent Heat Absorbent Are Combined, Oct. 31 2000, JPO, Abstract.*

(Continued)

*Primary Examiner* — David Sample
*Assistant Examiner* — Tahseen N Khan
(74) *Attorney, Agent, or Firm* — Dority & Manning, P.A.

(57) ABSTRACT

A cooling product (e.g., pad, bandage, headband, wrap, cloth, and so forth) that contains a gel configured to cool the skin of a body part when placed adjacent thereto is provided. The gel is contained within a composite that has two or more fibrous layers structured to provide enhanced distribution of the gel therethrough. More specifically, a first fibrous layer may rapidly distribute the gel in primarily the -z direction (direction of thickness) to a second fibrous layer, which then distributes it primarily in the -x and -y directions. The second fibrous layer may then be placed adjacent to a user's skin to provide the desired cooling. Because the gel is distributed primarily in the -x and -y directions, however, direct contact between the gel and skin is limited, thereby reducing the "sticky" feel normally associate with such gels. The cooling product is also flexible, and may be easily adapted to a body part.

25 Claims, 3 Drawing Sheets

U.S. PATENT DOCUMENTS

| | | | |
|---|---|---|---|
| 4,404,820 A * | 9/1983 | Romaine | 62/530 |
| 4,499,154 A | 2/1985 | James et al. | |
| 4,516,564 A | 5/1985 | Koiso et al. | |
| 4,747,841 A | 5/1988 | Kuratomi et al. | |
| 4,756,299 A | 7/1988 | Podella | |
| 4,789,592 A | 12/1988 | Taniguchi et al. | |
| 4,795,668 A | 1/1989 | Krueger et al. | |
| 4,925,603 A * | 5/1990 | Nambu | 264/28 |
| 4,925,743 A | 5/1990 | Ikeda et al. | |
| 5,057,368 A | 10/1991 | Largman et al. | |
| 5,069,970 A | 12/1991 | Largman et al. | |
| 5,108,820 A | 4/1992 | Kaneko et al. | |
| 5,162,074 A | 11/1992 | Hills | |
| 5,178,139 A | 1/1993 | Angelillo et al. | |
| 5,277,976 A | 1/1994 | Hogle et al. | |
| 5,284,703 A | 2/1994 | Everhart et al. | |
| 5,336,552 A | 8/1994 | Strack et al. | |
| 5,350,624 A | 9/1994 | Georger et al. | |
| 5,366,491 A | 11/1994 | Ingram et al. | |
| 5,382,400 A | 1/1995 | Pike et al. | |
| 5,398,667 A | 3/1995 | Witt | |
| 5,407,741 A | 4/1995 | Ota | |
| 5,425,975 A | 6/1995 | Koiso et al. | |
| 5,454,363 A | 10/1995 | Sata | |
| 5,466,410 A | 11/1995 | Hills | |
| 5,509,915 A * | 4/1996 | Hanson et al. | 604/378 |
| 5,527,892 A | 6/1996 | Borsotti et al. | |
| RE35,427 E | 1/1997 | Poettgen | |
| 5,620,779 A | 4/1997 | Levy et al. | |
| 5,667,625 A * | 9/1997 | Alikhan | 156/553 |
| 5,681,298 A | 10/1997 | Brunner et al. | |
| 5,702,375 A | 12/1997 | Angelillo et al. | |
| D390,708 S | 2/1998 | Brown | |
| 5,770,528 A | 6/1998 | Mumick et al. | |
| 5,770,543 A | 6/1998 | Garst et al. | |
| 5,817,394 A * | 10/1998 | Alikhan et al. | 428/137 |
| 5,879,343 A * | 3/1999 | Dodge et al. | 604/378 |
| 5,879,378 A | 3/1999 | Usui | |
| 5,918,590 A | 7/1999 | Burkett et al. | |
| 5,925,072 A | 7/1999 | Cramer et al. | |
| 5,962,112 A | 10/1999 | Haynes et al. | |
| 5,975,074 A | 11/1999 | Koiso et al. | |
| 5,984,995 A | 11/1999 | White | |
| 6,019,782 A | 2/2000 | Davis et al. | |
| D428,267 S | 7/2000 | Romano, III et al. | |
| 6,093,665 A | 7/2000 | Sayovitz et al. | |
| 6,099,555 A | 8/2000 | Sabin | |
| 6,099,556 A | 8/2000 | Usui | |
| 6,127,294 A | 10/2000 | Koiso et al. | |
| 6,164,487 A | 12/2000 | Hicks | |
| 6,197,045 B1 | 3/2001 | Carson | |
| 6,200,669 B1 | 3/2001 | Marmon et al. | |
| 6,264,681 B1 | 7/2001 | Usui | |
| 6,265,631 B1 | 7/2001 | Angelillo et al. | |
| 6,290,091 B1 | 9/2001 | Bell | |
| 6,436,128 B1 | 8/2002 | Usui | |
| 6,444,199 B1 * | 9/2002 | Renn | 424/78.26 |
| 6,642,427 B2 | 11/2003 | Roe et al. | |
| 6,648,909 B2 | 11/2003 | Helming | |
| 6,723,892 B1 | 4/2004 | Daley et al. | |
| 6,727,196 B2 | 4/2004 | Yahiaoui et al. | |
| 6,770,064 B1 | 8/2004 | Ruscher | |
| 6,781,027 B2 * | 8/2004 | Fenwick et al. | 604/365 |
| 6,791,004 B2 | 9/2004 | Sprengard-Eichel et al. | |
| 6,863,682 B2 | 3/2005 | Usui | |
| 7,081,211 B2 | 7/2006 | Li et al. | |
| 7,419,677 B2 | 9/2008 | Gueret | |
| 2002/0142027 A1 * | 10/2002 | Gueret | 424/443 |
| 2002/0161420 A1 | 10/2002 | Usui | |
| 2003/0075549 A1 | 4/2003 | O'Brien et al. | |
| 2004/0063603 A1 | 4/2004 | Dave et al. | |
| 2004/0115412 A1 * | 6/2004 | Baron et al. | 428/214 |
| 2004/0138598 A1 | 7/2004 | Kortuem et al. | |
| 2004/0178384 A1 | 9/2004 | Usui | |
| 2005/0028806 A1 | 2/2005 | Kumamoto et al. | |
| 2005/0136765 A1 | 6/2005 | Shannon | |
| 2005/0136773 A1 * | 6/2005 | Yahiaoui et al. | 442/394 |
| 2005/0136965 A1 | 6/2005 | Fourestie et al. | |
| 2006/0141882 A1 | 6/2006 | Quincy, III et al. | |
| 2006/0142712 A1 | 6/2006 | Quincy, III et al. | |
| 2006/0142828 A1 | 6/2006 | Schorr et al. | |
| 2006/0276863 A1 | 12/2006 | Kumamoto et al. | |
| 2007/0074326 A1 | 4/2007 | Komechak | |
| 2007/0077331 A1 | 4/2007 | Kiefer et al. | |
| 2007/0141929 A1 | 6/2007 | Quincy, III et al. | |
| 2007/0142883 A1 | 6/2007 | Quincy, III et al. | |
| 2007/0156213 A1 | 7/2007 | Friedensohn et al. | |

FOREIGN PATENT DOCUMENTS

| | | |
|---|---|---|
| EP | 0427475 A1 | 5/1991 |
| EP | 0786240 A1 | 7/1997 |
| EP | 0856302 A1 | 8/1998 |
| EP | 1112702 A1 | 7/2001 |
| EP | 1566156 A1 | 8/2005 |
| GB | 316878 | 6/1930 |
| GB | 2297490 A | 8/1996 |
| GB | 2312846 A | 11/1997 |
| JP | 2000300594 A * | 10/2000 |
| JP | 2003245298 A * | 9/2003 |
| WO | WO9829079 A1 | 7/1998 |
| WO | WO9909918 A1 | 3/1999 |
| WO | WO0103619 A1 | 1/2001 |
| WO | WO2004105709 A1 | 12/2004 |
| WO | WO2007028023 A2 | 3/2007 |

OTHER PUBLICATIONS

Machine English Translation of JP 2003/245298, Yokoi Shusuke, Cooling Appliance, Sep. 2, 2003, JPO, whole document.*

Search Report and Written Opinion for PCT/IB2008/050800 dated Nov. 12, 2008.

* cited by examiner

US 8,187,697 B2

COOLING PRODUCT

BACKGROUND OF THE INVENTION

Cooling products are used for a wide variety of purposes, such as for cooling a body part (e.g., forehead, cheek, jaws, etc.) of a person who is feverish, injured, etc. Simple ice packs, for instance, are often used to help reduce swelling. However, ice packs do not normally permit compression on and around the injured area so as to achieve the best possible minimization of swelling. Further, when an ice pack is applied, the injured person has little freedom of movement. In an attempt to overcome these problems, wraps have been developed that are more flexible in nature. One example of such a wrap is described in U.S. Pat. No. 4,377,160 to Romaine. More specifically, this wrap contains a gel-like material formed by gelling a polyvinyl alcohol solution. A sheet or strip of thin polyurethane foam is dipped in the polyvinyl alcohol solution and thereafter dipped in a reactive gelling agent solution, such as an aqueous borax solution, to form a gel. Despite the benefits of such gel-like cooling products, a variety of problems nevertheless remain. For example, these products often possess a "sticky" feel due to the adhesive nature of the gel and its close proximity to a user's skin.

As such, a need currently exists for an improved cooling product that is flexible, effective, and relatively non-tacky.

SUMMARY OF THE INVENTION

In accordance with one embodiment of the present invention, a cooling product is disclosed for reducing the temperature of a user's skin. The cooling product comprises a composite that includes a first fibrous layer and a second fibrous layer, the permeability of the first fibrous layer being greater than the permeability of the second fibrous layer. The product further comprises a gel distributed through the first fibrous layer and the second fibrous layer of the composite. The gel is formed from a crosslinked network comprising a gelling polymer.

In accordance with another embodiment of the present invention, a method for forming a cooling product is disclosed. The method comprises applying a first coating formulation to the first fibrous layer of a composite so that at least a portion of the formulation flows through the first fibrous layer and into a second fibrous layer of the composite. The permeability of the first fibrous layer is greater than the permeability of the second fibrous layer, and the first coating formulation comprises a gelling polymer. The method also comprises applying a second coating formulation to the first fibrous layer, the second fibrous layer, or both. The second coating formulation comprises a crosslinking agent. The crosslinking agent and the gelling polymer react to form a crosslinked network.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Definitions

Figure 1:
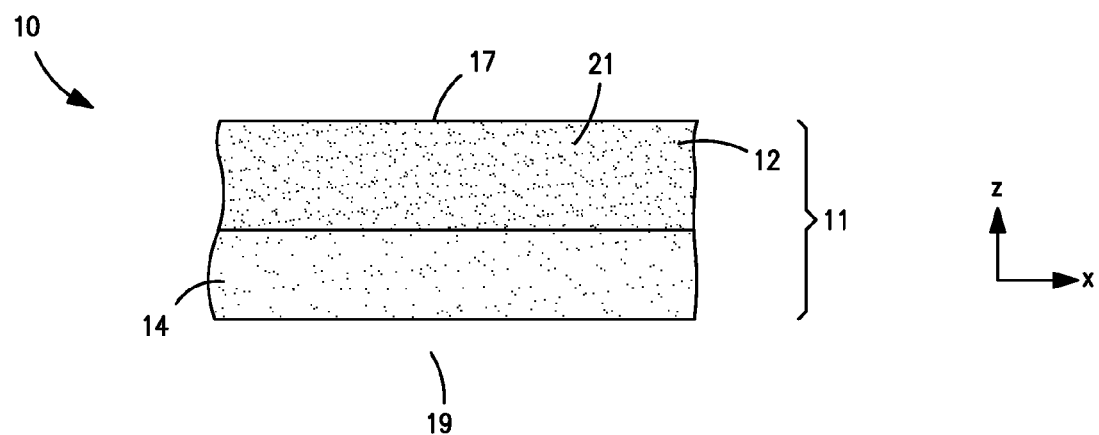
FIG. 1 illustrates a cross-sectional view of one embodiment of a cooling product of the present invention.

As used herein the term "nonwoven" web or layer means a web having a structure of individual fibers or threads which are interlaid, but not in an identifiable manner as in a knitted fabric. Nonwoven webs may include, for instance, meltblown webs, spunbond webs, airlaid webs, carded webs, hydraulically entangled webs, etc.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Buntin, et al., which is incorporated herein in its entirety by reference thereto for all purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 micrometers, and are often between about 5 to about 20 micrometers.

As used herein, the term "coform" generally refers to a composite material that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

Permeability:

The "du Plessis" Permeability may be calculated from the following equation:

$$\text{Permeability} = 0.051 \cdot R \cdot (1-\text{Porosity}) \cdot (\text{Porosity}/[1-\text{Porosity}])^{2.75}$$

wherein,

R is the fiber radius; and

Porosity = (1−web density)/fiber density

Reference for the porosity equation may be found in the article "Quantification of Unidirectional Fiber Bed Permeability" by J. Westhuizen and J. P. du Plessis in the Journal of Composite Materials, 28(7), 1994, which is incorporated herein in its entirety by reference thereto for all purposes.

Permeability may also be calculated from the Kozeny-Carman equation, such as described in detail in U.S. Pat. No. 5,879,343 to Dodge II, et al.; U.S. Pat. No. 6,723,892 to Daley, et al.; an article by R. W. Hoyland and R. Field in the Journal Paper Technology and Industry, December 1976, p. 291-299 and Porous Media Fluid Transport and Pore Structure by F. A. L. Dullien, 1979, Academic Press, Inc. ISBN 0-12-223650-5, all of which are incorporated herein in their entirety by reference thereto for all purposes. The Kozeny-Carman equation is set forth below:

| Calculated Variable | | Equation | Dimensions |
|---|---|---|---|
| Permeability = | k | $= \dfrac{\varepsilon^3}{KS_0^2(1-\varepsilon)^2} \dfrac{1}{9.87 \times 10^{-9}}$ | Darcys |
| | | | dimensionless |
| | | | cm²/g |
| | | | g/cm³ |
| | | | cm⁻¹ |
| Kozeny Constant = | k | $= \dfrac{3.5\varepsilon^3}{(1-\varepsilon)^{0.5}}[1 + 57(1-\varepsilon)^3]$ | |
| Surface area per mass of the material | $S_V$ | $= \sum_i \dfrac{x_i}{r_{i,eff}\rho_i}$ | |
| Mass weighted average component density | $\rho_{avg}$ | $= \left(\sum_i \dfrac{x_i}{\rho_i}\right)^{-1}$ | |
| Surface area per solid volume of the material | $S_0$ | $= S_V \rho_{avg}$ | |
| Porosity = | $\varepsilon$ | $= 1 - \sum_i x_i \dfrac{\rho_{web}}{\rho_i}$ | dimensionless |
| | | | cm |
| | | | g/cm³ |

| Calculated Variable | | Equation | Dimensions |
|---|---|---|---|
| Effective fiber radius = | $r_{i,eff}$ | $= \dfrac{V_i}{SA_i}$ | |
| Density of web = | $\rho_{web}$ | $= \dfrac{BW}{10^3 \cdot t}$ | |
| for long cylinders = | $r_{i,eff}$ | $= \dfrac{\frac{\pi d_i^2 L}{4}}{\pi d_i L} = \dfrac{d_i}{4 \times 10^4}$ | |
| for spheres = | $r_{i,eff}$ | $= \dfrac{\frac{4}{3}\frac{\pi d_i^3}{8}}{\pi d_i^2} = \dfrac{d_i}{6 \times 10^4}$ | | where $d_i$ = diameter of component i (microns)

$\rho_i$ = density of component i (g/cm³)

$x_i$ = mass fraction of component i in web

BW = weight of sample/area (g/m²)

t = thickness of sample (mm) under 0.05 psi (23.9 dyne/cm²) or 2.39 Pascal (N/m²) load Permeability Example Calculation For a structure which contains 57% southern softwood pulp, 40% superabsorbent and 3% binder fiber, and has a basis weight of 617.58 g/m² and a bulk thickness of 5.97 mm at 0.05 psi the example permeability calculation follows.

The component properties are as follows (note shape is approximated):

| Component | Shape | Diameter $d_i$ (microns) | Density $\rho_i$ (g/cm³) | Mass Fraction $x_i$ |
|---|---|---|---|---|
| Southern softwood | Cylinder | 13.3 | 1.55 | 0.57 |
| Superabsorbent | Sphere | 1125 | 1.50 | 0.40 |
| Binder | Cylinder | 17.5 | 0.925 | 0.03 |

$$\rho_{web}(g/cm^3) = \dfrac{BW}{10^3 \cdot t}$$

$$\rho_{web}(g/cm^3) = \dfrac{617.58}{(5.97)10^3}$$

$$\rho_{web}(g/cm^3) = 0.1034$$

$$\varepsilon = 1 - \sum_i x_i \dfrac{\rho_{web}}{\rho_i}$$

$$\varepsilon = 1 - 0.57 \dfrac{0.1034}{1.55} - 0.40 \dfrac{0.1034}{1.49} - 0.03 \dfrac{0.1034}{0.925}$$

$$\varepsilon = 0.9309$$

$$S_V(cm^2/g) = \sum_i \dfrac{x_i}{r_{i,eff}\rho_i}$$

$$S_V(cm^2/g) = \dfrac{0.57}{\left(\dfrac{13.3}{4\times 10^4}\right)\times 1.55} + \dfrac{0.40}{\left(\dfrac{1125}{6\times 10^4}\right)\times 1.49} + \dfrac{0.03}{\left(\dfrac{17.5}{4\times 10^4}\right)\times 0.925}$$

$$S_V(cm^2/g) = 1194$$

$$\rho_{avg}(g/cm^3) = \left(\sum_i \dfrac{x_i}{\rho_i}\right)^{-1}$$

$$\rho_{avg}(g/cm^3) = \left(\dfrac{0.57}{1.55} + \dfrac{0.40}{1.49} + \dfrac{0.03}{0.925}\right)^{-1}$$

$$\rho_{avg}(g/cm^3) = 1.496$$

-continued $$S_0(cm^{-1}) = S_V \rho_{avg}$$

$$S_0(cm^{-1}) = 1194 \times 1.496$$

$$S_0(cm^{-1}) = 1786$$

$$K = \frac{3.5\varepsilon^3}{(1-\varepsilon)^{0.5}}[1 + 57(1-\varepsilon)^3]$$

$$K = \frac{3.5(0.9309)^3}{(1-0.9309)^{0.5}}[1 + 57(1-0.9309)^3]$$

$$K = 10.94$$

$$k = \frac{\varepsilon^3}{KS_0^3(1-\varepsilon)^2}\frac{1}{9.87 \times 10^{-9}}$$

$$k = \frac{(0.9309)^3}{(10.94)(1786)^2(1-0.9309)^2}\frac{1}{9.87 \times 10^{-9}}$$

$$k = 491 \text{ darcys}$$

In the example above, the duPlessis permeability is likewise about 822 darcys.

Caliper:

The caliper (or bulk thickness) of a material is a measure of thickness and may be measured at 0.05 psi with a Starret-type bulk tester, in units of millimeters.

Density:

The density is calculated by dividing the weight per unit area of a sample in grams per square meter (gsm) by the caliper of the sample in millimeters (mm) at 68.9 Pascals, and multiplying the result by 0.001 to convert the value to grams per cubic centimeter (g/cc).

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations.

Generally speaking, the present invention is directed to a cooling product (e.g., pad, bandage, headband, wrap, cloth, and so forth) that contains a gel configured to cool the skin of a body part when placed adjacent thereto. The gel is contained within a composite that has two or more fibrous layers structured to provide enhanced distribution of the gel therethrough. More specifically, a first fibrous layer may rapidly distribute the gel in primarily the -z direction (direction of thickness) to a second fibrous layer, which then distributes it primarily in the -x and -y directions. The second fibrous layer may then be placed adjacent to a user's skin to provide the desired cooling. Because the gel is distributed primarily in the -x and -y directions, however, direct contact between the gel and skin is limited, thereby reducing the "sticky" feel normally associate with such gels. The cooling product is also flexible, and may be easily adapted to a body part.

I. Gel

The gel of the present invention is formed from a crosslinked network that includes one or more gelling polymers. Such polymers may be formed from at least one monomer that is hydrophilic and water-soluble. Some examples of such monomers include, but are not limited to, vinyl pyrrolidone, hydroxyethyl acrylate or methacrylate (e.g., 2-hydroxyethyl methacrylate), hydroxypropyl acrylate or methacrylate, acrylic or methacrylic acid, acrylic or methacrylic esters or vinyl pyridine, acrylamide, vinyl alcohol, ethylene oxide, derivatives thereof, and so forth. Other examples of suitable monomers are described in U.S. Pat. No. 4,499,154 to James, et al., which is incorporated herein in its entirety by reference thereto for all purposes. The resulting polymers may be homopolymers or interpolymers (e.g., copolymer, terpolymer, etc.), and may be nonionic, anionic, cationic, or amphoteric. In addition, the polymer may be of one type (i.e., homogeneous), or mixtures of different polymers may be used (i.e., heterogeneous). In one particular embodiment, the gelling polymer contains a repeating unit having a functional hydroxyl group, such as polyvinyl alcohol ("PVOH"), copolymers of polyvinyl alcohol (e.g., ethylene vinyl alcohol copolymers, methyl methacrylate vinyl alcohol copolymers, etc.), etc. Vinyl alcohol polymers, for instance, have at least two or more vinyl alcohol units in the molecule and may be a homopolymer of vinyl alcohol, or a copolymer containing other monomer units. Vinyl alcohol homopolymers may be obtained by hydrolysis of a vinyl ester polymer, such as vinyl formate, vinyl acetate, vinyl propionate, etc. Vinyl alcohol copolymers may be obtained by hydrolysis of a copolymer of a vinyl ester with an olefin having 2 to 30 carbon atoms, such as ethylene, propylene, 1-butene, etc.; an unsaturated carboxylic acid having 3 to 30 carbon atoms, such as acrylic acid, methacrylic acid, crotonic acid, maleic acid, fumaric acid, etc., or an ester, salt, anhydride or amide thereof; an unsaturated nitrile having 3 to 30 carbon atoms, such as acrylonitrile, methacrylonitrile, etc.; a vinyl ether having 3 to 30 carbon atoms, such as methyl vinyl ether, ethyl vinyl ether, etc.; and so forth.

The degree of hydrolysis may be selected to optimize the cooling properties, solubility, etc., of the polymer. For example, the degree of hydrolysis may be about 90 mole % or greater, in some embodiments about 95 mole % or greater, and in some embodiments, about 99 mole % or more. Such an elevated degree of hydrolysis lowers the solubility of the polymer in water so that it may absorb a greater amount of water to enhance the cooling effect. Examples of suitable highly hydrolyzed polyvinyl alcohol polymers are available under the designation CELVOL™ 165 or 125 from Celanese Corp. If desired, such highly hydrolyzed polyvinyl alcohol polymers may be blended with partially hydrolyzed polymers to improve water solubility. The degree of hydrolysis of such polymers may be less than about 90 mole %, and in some embodiments, from about 85 mole % to about 89 mole %. Examples of suitable partially hydrolyzed polyvinyl alcohol polymers are available under the designation CELVOL™ 203, 205, 502, 504, 508, 513, 518, 523, 530, or 540 from Celanese Corp. When employed, the weight ratio of the partially hydrolyzed to highly hydrolyzed polymers is typically from about 0.1 to about 50, in some embodiments from about 0.5 to about 20, and in some embodiments, from about 1 to about 5. Regardless of the type of polymers employed, however, the concentration of gelling polymer(s) in the gel (based on wt. % of solids) is typically from about 30 wt. % to about 90 wt. %, in some embodiments from about 35 wt. % to about 80 wt. %, and in some embodiments, from about 40 wt. % to about 70 wt. %.

Any known crosslinking technique may be employed in the present invention, including known ionic or covalent crosslinking techniques. Ionic crosslinking may be induced by contacting the gelling polymer with an ionic crosslinking agent, such as those containing borate, carbonate, sulfate, and other ions. Borate ions, for example, may form strong hydrogen bonds with the hydroxyl groups of the polymer, and thus forms hydrogen-bonded crosslinks between the polymer molecules. Specific examples of suitable ionic crosslinking agents for use in the present invention include sodium tetraborate (e.g., anhydrous sodium tetraborate, sodium tetraborate pentahydrate, sodium tetraborate decahydrate, etc.), potassium tetraborate, sodium carbonate, ammonium sulfate, sodium sulfate, potassium sulfate, aluminum sulfate, zinc sulfate, etc. The concentration of crosslinking agent(s) in the gel (based on wt.% of solids) is typically from about 1 wt. % to about 35 wt. %, in some embodiments from about 5 wt. % to about 30 wt. %, and in some embodiments, from about 10 wt. % to about 25 wt. %.

Although not required, the gel desirably acts as a pressure-sensitive adhesive to improve the self-adhering nature of the cooling product. In this regard, the gel may also contain a plasticizer. Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, glycerol, and sorbitol), polyols (e.g., ethylene glycol, propylene glycol, dipropylene glycol, butylene glycol, and hexane triol), etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as ethylene acrylic acid, ethylene maleic acid, butadiene acrylic acid, butadiene maleic acid, propylene acrylic acid, propylene maleic acid, and other hydrocarbon based acids. Glycerol is particularly suitable due to its high compatibility with polyvinyl alcohol, high boiling point, and low volatility. The concentration of plasticizer(s) in the gel (based on wt. % of solids) is typically from about 1 wt. % to about 35 wt. %, in some embodiments from about 5 wt. % to about 30 wt. %, and in some embodiments, from about 10 wt. % to about 25 wt. %.

Cooling agents may also be provided in the gel that enhance the physiological cooling sensation to a user. Exemplary cooling agents include menthol, icilin, isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint oil, peppermint oil, menthone, menthone glycerol ketal, menthyl lactate, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, and menthyl pyrrolidone carboxylate. Other suitable cooling agents are described in 2007/0077331 to Kiefer, et al., which is incorporated herein in its entirety by reference thereto for all purposes. The concentration of cooling agent(s) in the gel (based on wt. % of solids) is typically from about 1 wt. % to about 35 wt. %, in some embodiments from about 5 wt. % to about 30 wt. %, and in some embodiments, from about 10 wt. % to about 25 wt. %.

The gel may also contain a preservative or preservative system to inhibit the growth of microorganisms over an extended period of time. Suitable preservatives for use in the present compositions may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. One suitable preservative is Kathon® LX, which is a mixture of methylchloroisothiazolinone and methylisothiazolinone available from Rohm & Haas. Still another suitable preservative is Dowicil 75, which contains 1-(3-chloroallyl)-3,5,7-triaza-1-azoniaadamantane chloride and is available from Dow Chemical Co. of Midland, Mich. The concentration of preservative(s) in the gel (based on wt. % of solids) is typically from about 0.001 wt. % to about 10 wt. %, in some embodiments from about 0.01 wt. % to about 5 wt. %, and in some embodiments, from about 0.1 wt. % to about 4 wt. %.

In addition to the above-mentioned components, other components, such as surfactants, pH adjusters, binders, dyes/pigments/inks, viscosity modifiers, etc., may also be included in the gel of the present invention. When employed, such hadditional components typically constitute from about 0.001 wt. % to about 10 wt. %, and in some embodiments, from about 0.1 wt. % to about 5 wt. % of the gel.

The manner in which the gel is applied to the composite of the present invention may vary. For example, one or more components of the gel (e.g., gelling polymer, crosslinking agent, etc.) may be initially dissolved or dispersed in a solvent to form a coating formulation. Suitable solvents may include water; alcohols, such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. In one particular embodiment, for example, water is used as the solvent so that an aqueous coating formulation is formed. Although the actual concentration of solvent (e.g., water) employed will generally depend on the type of components and the composite on which it is applied, it is nonetheless typically present in an amount from about 30 wt. % to about 99 wt. %, in some embodiments from about 50 wt. % to about 98 wt. %, and in some embodiments, from about 60 wt. % to about 95 wt. % of the coating formulation.

The gelling polymer and crosslinking agent may be mixed together to form a coating formulation that is then applied to the composite. More desirably, however, the gelling polymer and crosslinking agent are applied as separate formulations to inhibit premature gelling prior to application to the composite. For example, the gelling polymer may be applied to the composite in a first coating formulation and the crosslinking agent may thereafter be applied in a second coating formulation. Of course, the second coating formulation may also be applied to composite prior to the first coating formulation. The gelling polymer typically constitutes from about 0.1 wt. % to about 20 wt. %, in some embodiments from about 0.5 wt. % to about 15 wt. %, and in some embodiments, from about 1 wt. % to about 10 wt. % of the first coating formulation. Likewise, the crosslinking agent typically constitutes from about 0.1 wt. % to about 20 wt. %, in some embodiments from about 0.5 wt. % to about 15 wt. %, and in some embodiments, from about 1 wt. % to about 10 wt. % of the second coating formulation. Other components (e.g., plasticizer, cooling agent, preservative, etc.) may be added to one or both of the formulations as desired.

The solids content and/or viscosity of the coating formulation(s) may be varied to achieve the desired amount of cooling. For example, the coating formulation(s) may have a solids content of from about 0.5% to about 25%, in some embodiments from about 1% to about 20%, and in some embodiments, from about 5% to about 15%. By varying the solids content, the presence of the gelling polymer and/or crosslinking agent may be controlled. In addition, the viscosity of the coating formulation(s) may also vary depending on the coating method employed. For instance, lower viscosities may be employed for saturation coating techniques (e.g., dip-coating), while higher viscosities may be employed for drop-coating techniques. Generally, the viscosity is less than about 8000 centipoise, in some embodiments less than about 5000 centipoise, and in some embodiments, from about 50 to about 1000 centipoise, such as measured with a Brookfield DV-1 viscometer with an LV-4 spindle set at 100 rpm. If desired, thickeners or other viscosity modifiers may be employed to increase or decrease viscosity.

The coating formulation(s) may be applied using any conventional technique, such as bar, roll, knife, curtain, print (e.g., rotogravure), spray, slot-die, drop-coating, or dip-coating techniques. Upon application, it is normally desired that the resulting gel coating possess a certain moisture content to facilitate its ability to provide cooling. The moisture content is typically from about 60 wt. % to about 99 wt. %, in some embodiments from about 75 wt. % to about 95 wt. %, and in some embodiments, from about 80 wt. % to about 90 wt. %. If desired, the composite may be dried to help achieve the desired moisture content. For example, the composite may be dried at a temperature of at least about 10° C., in some embodiments at least about 20° C., and in some embodiments, from about 20° C. to about 30° C. The add-on level of the gel may also be varied as desired. The "add-on level" is determined by subtracting the weight of the untreated composite from the weight of the treated composite, dividing this calculated weight by the weight of the untreated composite, and then multiplying by 100%. Lower add-on levels may optimize certain properties (e.g., reduced tackiness), while higher add-on levels may optimize cooling. In some embodiments, for example, the add-on level is from about 200% to about 5000%, in some embodiments from about 500% to about 2500%, and in some embodiments from about 800% to about 2000%.

Generally speaking, the coatings formulation(s) are applied to one or more surfaces of the composite. Typically, the coating formulation(s) are applied so that at least a portion flows through a first fibrous layer of the composite into a second fibrous layer. In one embodiment, for example, a first coating formulation containing the gelling polymer is applied to the first fibrous layer. Subsequently, a second formulation containing the crosslinking agent is then applied to the first and/or second fibrous layer. In this manner, for example, the resulting gel is distributed close enough to a user's skin to impart cooling, yet spaced apart from the surface to minimize the "sticky" feel of the cooling product.

Referring to FIG. 1, for example, one embodiment of a cooling product 10 that may be formed in accordance with the present invention is shown. As shown, the cooling product 10 defines two outer surfaces 17 and 19, and is in the form of a substantially flat, conformable, and foldable material. The overall size and shape of the cooling product 10 are not critical. For example, the cooling product 10 may have a shape that is generally triangular, square, rectangular, pentagonal, hexagonal, circular, elliptical, etc. Likewise, the cooling product 10 may have a relatively small total thickness. For example, the cooling product 10 may have a total thickness of from about 0.1 to about 100 millimeters, in some embodiments from about 0.5 to about 80 millimeters, and in some embodiments, from about 1 to about 50 millimeters.

Regardless, the cooling product 10 contains a composite 11 formed from a first fibrous layer 12 and a second fibrous layer 14. Any type of fibrous layers may generally be employed in the present invention, such as nonwoven webs, woven fabrics, knit fabrics, paper web, etc. When utilized, the nonwoven webs may include, but are not limited to, spunbonded webs (apertured or non-apertured), meltblown webs, carded webs (bonded or unbonded), airlaid webs, coform webs, hydraulically entangled webs, and so forth. A wide variety of polymers may be used, such as polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; and so forth.

Monocomponent and/or multicomponent fibers may be used to form the layers 12 and 14. Monocomponent fibers are generally formed from a polymer extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle. et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference thereto for all purposes.

Multicomponent fibers may, for instance, be desirable to help provide mechanical integrity and stabilization to the composite. Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 20% to about 80%, and in some embodiments, from about 40% to about 60% by weight of the low melting polymer. Further, the multicomponent fibers may have from about 80% to about 20%, and in some embodiments, from about 60% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The nonwoven web is optionally bonded using known techniques.

Although not necessarily required, the fibrous layer 12 and 14 are typically bonded together to form the composite structure. Any conventional bonding technique may be employed, such as through-air bonding, ultrasonic bonding, thermal point bonding, adhesive bonding, etc. For instance, the layers 12 and 14 may be through-air bonded during which air is forced through the layers and causes at least a portion of the fibers to melt or soften. The air is typically at a temperature above the melting temperature of one component of the fibers and below the melting temperature of another component. Alternatively, the layers 12 and 14 may be thermally bonded together at a plurality of discrete sites by passing the layers through two or more rolls, one or both of which are heated to melt-fuse the fibers. One or both of the rolls may also contain intermittently raised bond points to provide an intermittent bonding pattern. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., U.S. Design Pat. No. 428,267 to Romano et al. and U.S. Design Pat. No. 390,708 to Brown, which are incorporated herein in their entirety by reference thereto for all purposes.

Regardless of the particular manner in which the layers are constructed, the permeability (relates to the volume of voids or spaces per gram of fibers) of the first fibrous layer 12 is greater than that of the second fibrous layer 14 such that a permeability gradient is formed. In this manner, one or more coating formulations may initially enter the first fibrous layer 12 at a fast rate due to its large void sizes, but then be slowed by the small void sizes of the second fibrous layer 14 so that it does not penetrate completely therethrough. For example, a first coating formulation containing the gelling polymer may be applied to the surface 17 of the cooling product 10, which in this embodiment, is defined by the first fibrous layer 12. Consequently, the formulation may flow through the first fibrous layer 12 and into the second fibrous layer 14. Although the comparative low permeability of the second fibrous layer 14 forces a majority of the formulation in the -x and -y directions of the structure, at least a portion of the formulation flows through the layer 14. Thereafter, a second coating formulation containing the crosslinking agent may be applied to the surface 17 and/or 19. A gel 21 is thus formed that is distributed through the first and second fibrous layers 12 and 14 of the cooling product 10.

The permeability of the fibrous layers 12 and 14 may be expressed in terms of the Kozeny-Carman and/or du Plessis permeability, such as described above. For instance, the second fibrous layer 14 may have a Kozeny-Carman permeability of from about 300 to about 4000 Darcies, and in some embodiments, from about 500 to about 3000 Darcies, and a du Plessis permeability of from about 500 to about 6000 Darcies, and in some embodiments, from about 650 to about 4500 Darcies. Likewise, the first fibrous layer 12 may have a Kozeny-Carman permeability of from about 1,500 to about 20,000 Darcies, and in some embodiments, from about 3,000 to about 17,500 Darcies, and a du Plessis permeability of from about 2,500 to about 35,000 Darcies, and in some embodiments, from about 4,000 to about 30,000 Darcies. Although the actual permeability values may vary somewhat depending on the test method employed, the relative difference in permeabilities between the layers is substantially the same. That is, the first fibrous layer 12 has a permeability greater than the second fibrous layer 14. For example, the ratio of the permeability of the first fibrous layer 12 to the permeability of the second fibrous layer 14 may be about 1.5 or more, in some embodiments about 2.0 or more, and in some embodiments, from about 2.5 to about 8.0.

The basis weight and caliper (or bulk thickness) of the second fibrous layer 14 may be the same or different than the first fibrous layer 12. In some embodiments, the basis weight of the second fibrous layer 14 may be less than the first fibrous layer 12. For example, the second fibrous layer 14 may have a basis weight of from about 1 to about 100 gsm, in some embodiments, from about 5 to about 75 gsm, and in some embodiments, from about 10 to about 50 gsm. The first fibrous layer 12, on the other hand, may have a basis weight of from about 25 to about 2500 grams per square meter ("gsm"), in some embodiments from about 250 to about 300 gsm, and in some embodiments, from about 75 to about 250 gsm. Similarly, the caliper of the second fibrous layer 14 may also, be less than the first fibrous layer 12. For example the caliper of the second fibrous layer 14 may range from about 0.01 to about 1 millimeter ("mm"), in some embodiments from about 0.05 to about 0.75 mm, and in some embodiments, from about 0.1 to about 0.5 mm. The caliper of the first fibrous layer 12, on the other hand, may range from about 0.75 to about 10 mm, in some embodiments from about 1 to about 5 mm, and in some embodiments, from about 1.5 to about 4 mm.

The manner in which the permeability gradient across the layers 12 and 14 is created may generally vary. For example, the first and second fibrous layers 12 and 14 may be formed from substantially similar fibers. In such embodiments, the second fibrous layer 14 may be further densified to establish a permeability gradient through compaction or addition of other components, such as absorbent gelling material, superabsorbent polymers, silica, foam, thermobondable fibers, charcoal, zeolites, etc. Alternatively, the permeability gradient may be established by varying the fiber type, size, and so forth.

In one particular embodiment, the denier (i.e., coarseness or fineness) of the fibers may be varied to achieve the desired permeability gradient. Coarser fibers (i.e., those having higher deniers) are more resilient and less structurally compressive and thus allow for the creation of greater void volumes. In contrast, finer fibers (i.e., those having lower deniers) are less resilient and more structurally compressive and thus allow for the creation of greater compaction and fewer void volumes. In this regard, the first fibrous layer 12 may contain fibers of a higher denier than those of the second fibrous layer 14. Typically, the average denier of the fibers in the first fibrous layer 12 is greater than the average denier of the fibers in the second fibrous layer 14 such that the ratio of the average deniers is about 1.1 or more, in some embodiments about 1.5 or more, and in some embodiments, from about 2.0 to about 10.0. For example, the average denier of the fibers in the first fibrous layer 12 may range from about 3 to about 30, in some embodiments from about 5 to about 25, and in some embodiments, from about 8 to about 20. Likewise, the average denier of the fibers in the second fibrous layer 14 may range from about 0.1 to about 10, in some embodiments from about 0.5 to about 8, and in some embodiments, from about 1 to about 6.

Mixtures of small denier fibers and large denier fibers may also be used to further enhance liquid wicking and distribution properties. Namely, the use of differently sized fibers may result in the formation of voids of varying sizes and in multiple planes, which enhances intake and wicking of the coating formulation(s) used to form the gel 21. In one particular embodiment, for example, the first fibrous layer 12 contains a mixture of small and large denier fibers in which the small denier fibers have a denier of at least 2, in some embodiments at least 3, and in some embodiments, at least 5 less than the large denier fibers. For instance, the small denier fibers may have a denier of from about 2 to about 10, while the large denier fibers may have a denier of from about 4 to about 20. The relative percentage of the fibers may also vary. For example, the small denier fibers may constitute from about 25 wt. % to about 75 wt. %, and in some embodiments, from about 40 wt. % to about 60 wt. % of the fiber mixture. Likewise, the large denier fibers may constitute from about 25 wt. % to about 75 wt. %, and in some embodiments, from about 40 wt. % to about 60 wt. % of the fiber mixture. Although the second fibrous layer 14 may also contain a mixture of small and large denier fibers, it preferably contains fibers of approximately the same size so that they tend to form similarly sized pores in a single plane, thereby enhancing the -z directional barrier properties of the layer.

In one particular embodiment, the first fibrous layer 12 is a nonwoven web that contains a mixture of polyester staple fibers and polyethylene-polypropylene (sheath-core) bicomponent fibers. The second fibrous layer 14 may be a nonwoven web that contains polyethylene-polypropylene (sheath-core) bicomponent fibers. For instance, the first fibrous layer 12 may be a bonded carded web and the second fibrous layer may be a bonded or unbonded carded web. Various examples of such carded materials are described in U.S. Pat. No. 5,667,625 to Alikhan; U.S. Pat. No. 5,817,394 to Alikhan, et al.; and U.S. Pat. No. 6,781,027 to Fenwick, et al., which are incorporated herein in their entirety by reference thereto for all purposes.

The fibers of the layers 12 and 14 may be hydrophobic in nature and thus not readily receptive of the coating formulation(s) used to form the gel 21. However, the fibers may optionally be rendered hydrophilic through any known treatment for enhancing wettability. In one embodiment, for example, fibers of one or both layers may be applied with a treatment composition that contains a water-soluble organic polymer (e.g., polysaccharides and derivatives thereof) such as described above. The treatment composition may also employ surfactants to enhance the hydrophilic nature of the fibers. Ionic surfactants (i.e., anionic, cationic, or amphoteric surfactants) and/or nonionic surfactants may be employed in the treatment composition. Particularly suitable surfactants are nonionic surfactants, such as alkyl glycosides, ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

In one particular embodiment, alkyl glycosides are employed as a surface treatment for the fibers. Alkyl glycosides are generally prepared by reacting a monosaccharide, or a compound hydrolyzable to a monosaccharide, with an alcohol such as a fatty alcohol in an acid medium. For example, U.S. Pat. Nos. 5,527,892 and 5,770,543, which are incorporated herein in their entirety by reference thereto for all purposes, describe alkyl glycosides and/or methods for their preparation. Commercially available examples of suitable alkyl glycosides include Glucopon™ 220, 225, 425, 600 and 625, all of which are available from Cognis Corp. of Cincinnati, Ohio. These products are mixtures of alkyl mono- and oligoglucopyranosides with alkyl groups based on fatty alcohols derived from coconut and/or palm kernel oil. Glucopon™ 220, 225 and 425 are examples of particularly suitable alkyl polyglycosides. Glucopon™ 220 is an alkyl polyglycoside that contains an average of 1.4 glucosyl residues per molecule and a mixture of 8 and 10 carbon alkyl groups (average carbons per alkyl chain-9.1). Glucopon™ 225 is a related alkyl polyglycoside with linear alkyl groups having 8 or 10 carbon atoms (average alkyl chain-9.1 carbon atoms) in the alkyl chain. Glucopon™ 425 includes a mixture of alkyl polyglycosides that individually include an alkyl group with 8, 10, 12, 14 or 16 carbon atoms (average alkyl chain-10.3 carbon atoms). Glucopon™ 600 includes a mixture of alkyl polyglycosides that individually include an alkyl group with 12, 14 or 16 carbon atoms (average alkyl chain 12.8 carbon atoms). Glucopon™ 625 includes a mixture of alkyl polyglycosides that individually include an alkyl group having 12, 14 or 18 carbon atoms (average alkyl chain 12.8 carbon atoms). Still other suitable alkyl glycosides are available from Dow Chemical Co. of Midland, Mich. under the Triton™ designation, e.g., Triton™ CG-110 and BG-10.

The fibers may be applied with the treatment composition using any known application technique. Desirably, the fibers are treated before being incorporated into a web or combined with other fibers into a web. Suggested methods of treatment include, but are not limited to, saturation, spray, slot die, printing, foaming, and combinations and modifications thereof. In a saturation process, tows of fiber bundles are dipped in a bath containing the treating solution. Fibers are impregnated with treating solution and excess solution can optionally be removed by nipping between nip rolls. Alternatively, the treating solution is sprayed onto a tow of fibers followed by drying. The tows of fibers can be treated one time or several times in consecutive steps if desired. Also a combination of processes can also be used such as for example a saturation step followed by a spray of same or different chemical. Various other application techniques and treatment compositions are described in U.S. Patent Application Publication Nos. 2002/0069988 to Yahiaoui, et al. and 2005/0136773 to Yahiaoui, et al., which are incorporated herein in their entirety by reference thereto for all purposes.

Although various configurations of a cooling product have been described above, it should be understood that other configurations are also included within the scope of the present invention. For instance, other layers may also be employed to improve the properties of the cooling product. For example, a first composite may be employed in conjunction with a second composite. The composites may function together to provide cooling to a surface, or may each provide cooling to different surfaces.

Regardless of the particular construction employed, a cooling profile may be achieved for the cooling product in which a reduced temperature is reached quickly and maintained over an extended period of time. For example, a temperature reduction of at least about 1° C., in some embodiments at least about 2° C., and in some embodiments, at least about 3° C., may be achieved in 1 hour or less, and in some embodiments, 30 minutes or less. This reduced temperature may be substantially maintained for at least about 1 hour, in some embodiments at least about 2 hours, in some embodiments at least about 4 hours, and in some embodiments, at least about 10 hours (e.g., for overnight use).

The present invention may be better understood with reference to the following examples.

EXAMPLE 1

The ability to form a cooling substrate in accordance with the present invention was demonstrated. Initially, a two layer bonded carded web was provided. One side of the web contained 15 gsm of a 100% 3.0 denier FiberVisions ESC 233 bicomponent (PE sheath/PP core) fiber with 0.55% HR6 finish. The other side of the web contained 93 gsm of a blend of 50% 15 denier Invista T-295 polyester fiber with 0.50% L1 finish and 50% of a 6.0 denier FiberVisions ESC 236 bicomponent (PE sheath/PP core) fiber with 0.55% HR6 finish. The layers were formed using a pilot line having the capability of forming only a 50 gsm basis weight web. So, three separate webs were initially formed and laid on top of each other. Two of the webs, however, had the identical fiber content (i.e., 50% ESC 236 and 50% T-295) and the third web had a fiber content of 100% ESC 233. Accordingly, while three separate webs were initially formed, the resulting effect was a two layer composite. Various properties of the two layers and the resulting composite are set forth below in Table 1.

An aqueous formulation comprising a blend of polyvinyl alcohol was prepared as follows. In a 400 mL PYREX® beaker, 3.3 grams of Celvol™ 165 Polyvinyl Alcohol (Celanese), 10.0 grams of Celvol™ 523 Polyvinyl Alcohol (Celanese), 0.4 gram of benzoic acid (J. T. Baker), and 200.2 grams of distilled water were combined and stirred with propeller for about 15 minutes. Heat was applied to assist in dissolving the polyvinyl alcohol particles. The temperature was slowly increased to 60° C. after 20 minutes and to a peak temperature of 90 to 95° C. after about 1 hour. The peak temperature was held for about another 20 minutes before allowing the formulation to cool to room temperature. The following morning, the viscosity of the aqueous formulation was measured at about 644 centipoise using a Brookfield DV-1 viscometer with an LV-4 spindle set at 100 rpm. The calculated concentration of each component of the aqueous polyvinyl alcohol formulation is set forth below in Table 2.

TABLE 2

| Components of the Aqueous PVOH Formulation | |
|---|---|
| Component | Calculated Amount |
| Celvol ™ 165 Polyvinyl Alcohol | 1.5% |
| Celvol ™ 523 Polyvinyl Alcohol | 4.7% |
| Benzoic Acid | 0.2% |
| Water | 93.6% |

A second aqueous formulation comprising sodium tetraborate decahydrate (borax) and glycerol was prepared as follows. In a 250 mL PYREX® beaker, 5.0 grams of sodium tetraborate decahydrate (Aldrich A.C.S. reagent) and 5.1 grams of glycerol (Sigma-Aldrich A.C.S. reagent) were combined with 100.0 grams of distilled water. The aqueous borax formulation was stirred with propeller for about 20 minutes. The calculated concentration of each component of the aqueous borax formulation is set forth below in Table 3.

TABLE 3

| Components of the Aqueous Borax Formulation | |
|---|---|
| Component | Calculated Amount |
| Sodium Tetraborate Decahydrate | 4.5% |
| Glycerol | 4.6% |
| Water | 90.8% |

The aqueous polyvinyl alcohol formulation was applied first to the polyester/ bicomponent fiber side of a 6-inch by 5-inch piece of the two layer bonded carded web using a #60 single wound coating rod. Next, the aqueous borax formulation was applied using the same procedure. After the borax

TABLE 1

| | Properties of Fibrous Layers | | | | | | | |
|---|---|---|---|---|---|---|---|---|
| Layers | Kozeny-Carman Perm. (Darcies) | Ratio of Kozeny-Carman Perm. ($1^{st}/2^{nd}$) | du Plessis Perm. (Darcies) | Ratio of du Plessis Perm. ($1^{st}/2^{nd}$) | Basis Weight (gsm) | Bulk (mm) | Density (g/cm$^3$) | Fiber Diameter (μm) |
| $1^{st}$ | 7,275 | 6.3 | 12,754 | 8.2 | 93 | 3.90 | 0.024 | 47.7 (T-295) 30.7 (ESC 236) |
| $2^{nd}$ | 1,154 | | 1,552 | | 15 | 0.34 | 0.044 | 25.8 | application, there was evidence of a gel embedded within the fiber matrix of the web. The treated sample was then attached with clips to a horizontal wire and left for about 2.5 hours to allow some of the water to evaporate. Some additional water was then applied with a squeeze bottle to the surface and distributed throughout the sample with the coating rod, followed by about 40 minutes of additional dry time. These steps were taken to produce a substrate that felt uniformly cool to the skin without leaving any sticky residue. The weight of the substrate was recorded after each step of the procedure and is set forth below in Table 4.

TABLE 4

Substrate Content After Preparation Steps

| Preparation Step | Weight (grams) | Glycerol (grams) | Water (grams) | 165 PVOH (grams) | 523 PVOH (grams) | Benzoic Acid (grams) | Borax (grams) |
|---|---|---|---|---|---|---|---|
| Substrate before any treatment | 2.3 | 0 | 0 | 0 | 0 | 0 | 0 |
| After aqueous PVOH treatment | 33.4 | 0 | 29.1 | 0.47 | 1.46 | 0.06 | 0 |
| After aqueous Borax treatment | 51.2 | 0.82 | 45.3 | 0.47 | 1.46 | 0.06 | 0.80 |
| After 2.5 hours dry time | 23.4 | 0.82 | 17.5 | 0.47 | 1.46 | 0.06 | 0.80 |
| After exposure to water spray | 32.5 | 0.82 | 26.1 | 0.47 | 1.46 | 0.06 | 0.80 |
| After 40 minute dry time | 25.8 | 0.82 | 19.9 | 0.47 | 1.46 | 0.06 | 0.80 |
| Final gel wt. % | | 3.49% | 84.64% | 2.00% | 6.21% | 0.26% | 3.40% |

The substrate contained 23.51 grams of gel and the percent add-on was 1122%.

EXAMPLE 2

The ability to form a cooling substrate in accordance with the present invention was demonstrated. An aqueous formulation comprising a blend of polyvinyl alcohol and menthol was prepared as follows. In a 400 mL PYREX® beaker, 3.2 grams of Celvol™ 165 Polyvinyl Alcohol (Celanese), 10.0 grams of Celvol™ 523 Polyvinyl Alcohol (Celanese), and 199.5 grams of distilled water were combined and stirred with propeller for about 1 hour. Heat was applied to assist in dissolving the polyvinyl alcohol particles in a similar manner as described in Example 1. After the formulation had been stirred for about 35 minutes at 90-95° C., the heat was removed and 5.0 grams of menthol (Aldrich) was added. The aqueous polyvinyl alcohol and menthol formulation was stirred for about 10 minutes and then stored until the following morning. The viscosity was then measured at about 6920 centipoise using a Brookfield DV-1 viscometer with an LV-4 spindle set at 50 rpm. The calculated concentration of each component of the aqueous polyvinyl alcohol and menthol formulation is set forth below in Table 5.

TABLE 5

Components of the Aqueous PVOH + Menthol Formulation

| Component | Calculated Amount |
|---|---|
| Celvol ™ 165 Polyvinyl Alcohol | 1.5% |
| Celvol ™ 523 Polyvinyl Alcohol | 4.6% |
| Menthol | 2.3% |
| Water | 91.6% |

A second aqueous formulation comprising sodium tetraborate decahydrate (borax) and glycerol was prepared as follows. In a 250 mL PYREX® beaker, 4.8 grams of sodium tetraborate decahydrate (Aldrich A.C.S. reagent) and 5.0 grams of glycerol (Sigma-Aldrich A.C.S. reagent) were combined with 100.0 grams of distilled water. The aqueous borax formulation was stirred with spatula for several minutes to dissolve all components. The calculated concentration of each component of the aqueous borax formulation is set forth below in Table 6.

TABLE 6

Components of the Aqueous Borax Formulation

| Component | Calculated Amount |
|---|---|
| Sodium Tetraborate Decahydrate | 4.4% |
| Glycerol | 4.6% |
| Water | 91.0% |

The aqueous polyvinyl alcohol and menthol formulation was applied first to the polyester/bicomponent fiber side of a 6-inch by 5-inch piece of the two layer bonded carded web using a #60 single wound coating rod. Next, the aqueous borax formulation was applied using the same procedure. After the borax application, there was evidence of a gel embedded within the fiber matrix of the web. The treated sample was then attached with clips to a horizontal wire and left for about 2.5 hours to allow some of the water to evaporate. These steps were taken to produce a substrate that felt uniformly cool to the skin without leaving any sticky residue. The substrate also had a menthol fragrance. The weight of the substrate was recorded after each step of the procedure and is set forth below in Table 7.

TABLE 7

Substrate Content After Preparation Steps

| Preparation Step | Weight (grams) | Glycerol (grams) | Water (grams) | 165 PVOH (grams) | 523 PVOH (grams) | Menthol (grams) | Borax (grams) |
|---|---|---|---|---|---|---|---|
| Substrate before any treatment | 2.3 | 0 | 0 | 0 | 0 | 0 | 0 |
| After aqueous PVOH treatment | 34.2 | 0 | 29.2 | 0.48 | 1.47 | 0.73 | 0 |
| After aqueous Borax treatment | 47.3 | 0.60 | 41.1 | 0.48 | 1.47 | 0.73 | 0.58 |
| After 2.5 hours dry time | 28.6 | 0.60 | 22.4 | 0.48 | 1.47 | 0.73 | 0.58 |
| Final gel wt. % | | 2.28% | 85.30% | 1.83% | 5.60% | 2.78% | 2.21% |

The substrate contained 26.26 grams of gel and the percent add-on was 1242%.

EXAMPLE 3

Figure 2:
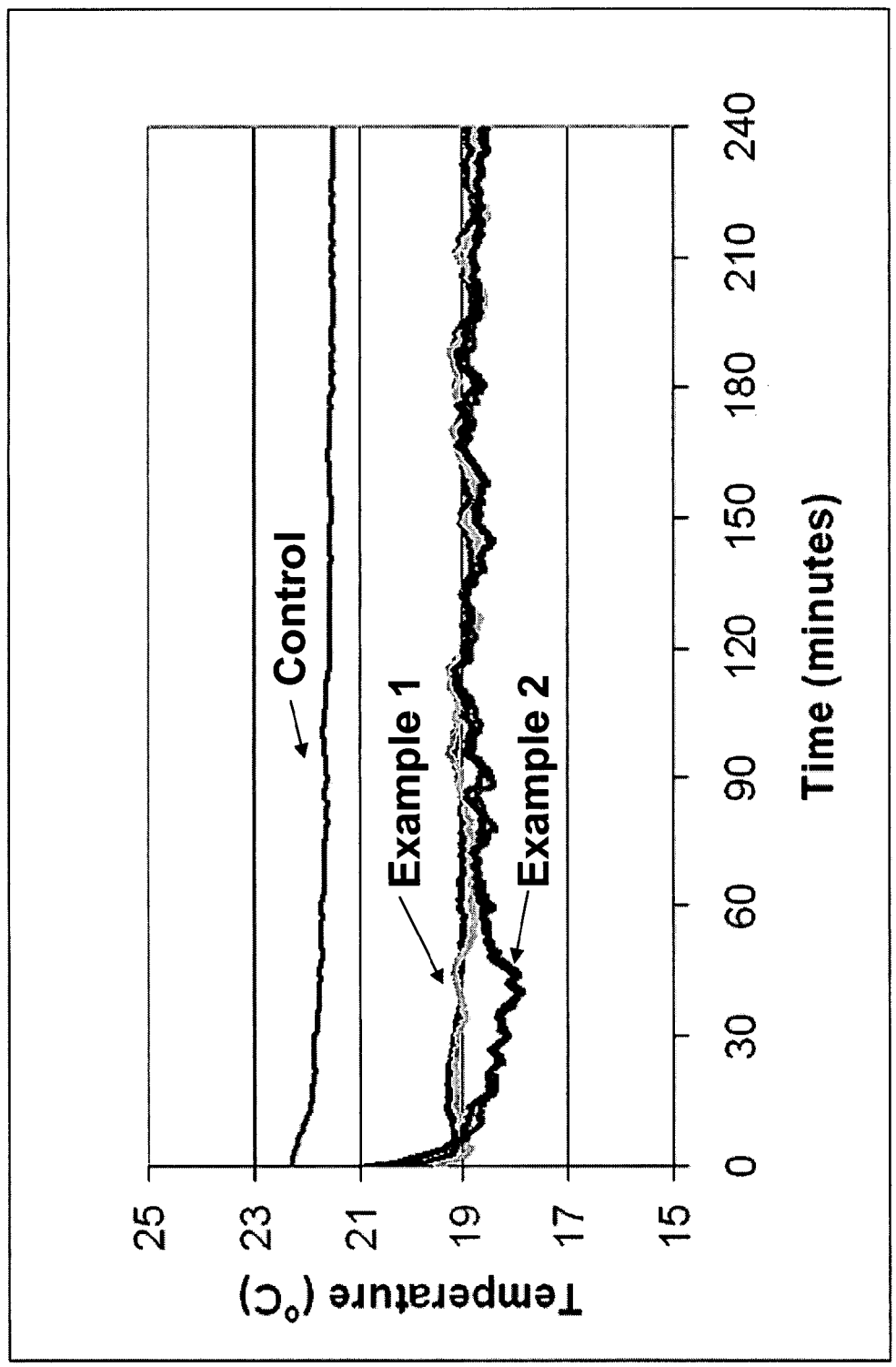
FIG. 2 is a thermal response curve showing temperature (° C.) versus time (minutes) for samples of Examples 1 and 2.

The ability to achieve a cooling response using the cooling substrates of the present invention was demonstrated. Specifically, the cooling substrates of Examples 1 and 2 were tested. Testing was conducted by attaching two thermocouples wired to a data collection device to the side of the substrates that contained 100% 3.0 denier FiberVisions ESC 233 bicomponent (PE sheath/PP core) fiber. A single thermocouple was attached to this same side of an untreated piece of the two layer bonded carded web to monitor the background or "control" temperature. The temperature was recorded as a function of time (at 5 second intervals) to give the thermal response curves shown in FIG. 2. It can be seen in FIG. 2 that both cooling substrates provide about a 3° C. drop in temperature relative to the control for the 4-hour time period shown. Data were actually collected for 10 hours and the same cooling response as shown in FIG. 2 occurred for both cooling substrates.

COMPARATIVE EXAMPLE

Figure 3:
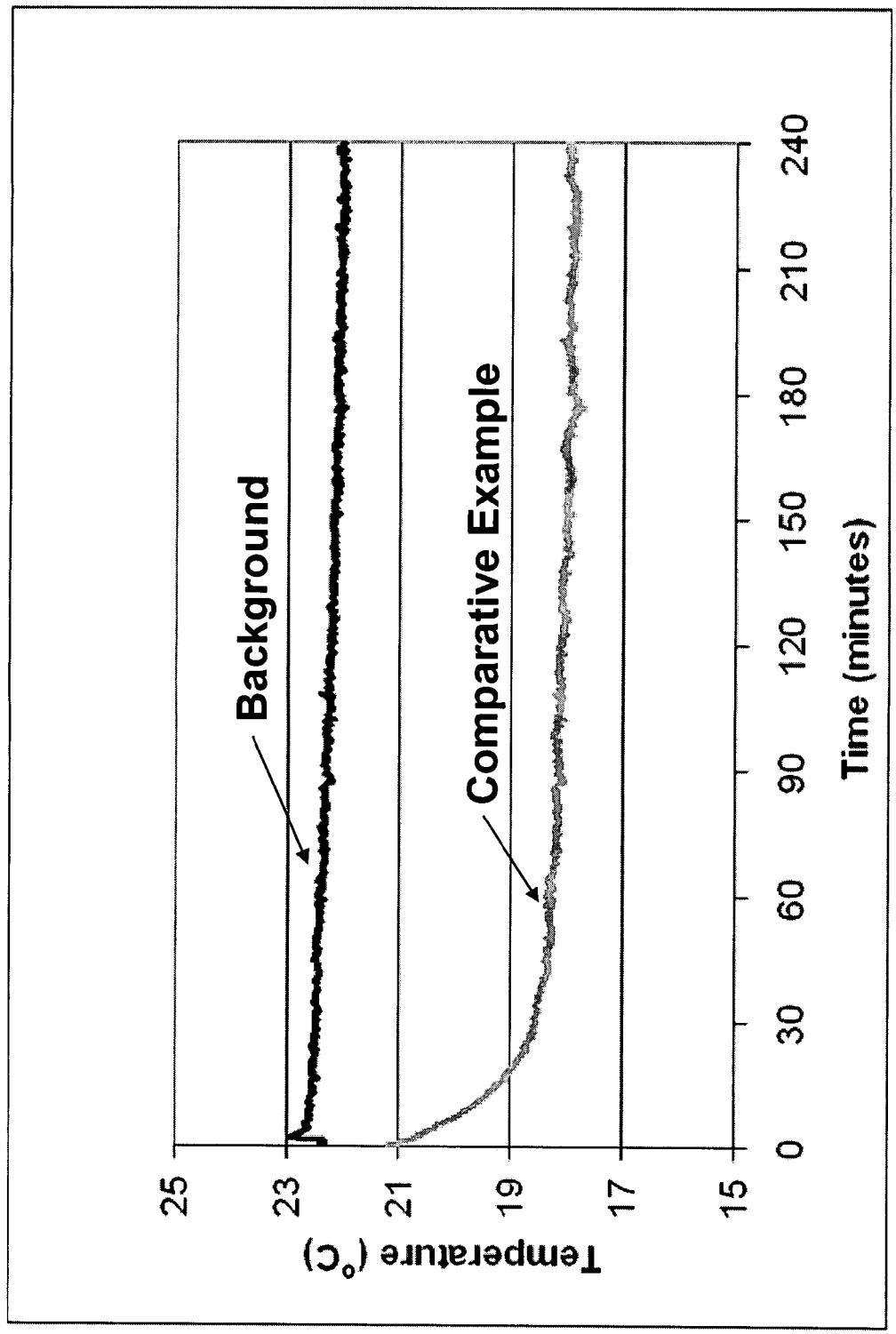
FIG. 3 is a thermal response curve showing temperature (° C.) versus time (minutes) for the Comparative Example.

FIG. 3 shows the cooling profile for an "Instant Cold Therapy Wrap" available from CVS® pharmacy. It is believed that this product is a polyvinyl alcohol hydrogel in an open cell foam as described in U.S. Pat. No. 4,377,160. The cooling profile (FIG. 3) is similar to that for the cooling substrates of Examples 1 and 2 (FIG. 2). However, unlike the cooling substrates of Examples 1 and 2, the CVS® product is quite sticky and can leave residue on the skin.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A cooling product for reducing the temperature of a user's skin, the cooling product comprising a composite that includes a first fibrous layer and a second fibrous layer, the permeability of the first fibrous layer being greater than the permeability of the second fibrous layer, the product further comprising a gel distributed through the first fibrous layer and the second fibrous layer of the composite, wherein the gel is formed from a crosslinked network comprising a gelling polymer and the add-on level of the gel is from about 200% to about 5000%.

2. The cooling product of claim 1, wherein the ratio of the permeability of the first fibrous layer to the permeability of the second fibrous layer is about 1.5 or more.

3. The cooling product of claim 1, wherein the ratio of the permeability of the first fibrous layer to the permeability of the second fibrous layer is from about 2.5 to about 8.0.

4. The cooling product of claim 1, wherein the Kozeny-Carman permeability of the first layer is from about 1,500 to about 20,000 Darcies and the Kozeny-Carman permeability of the second fibrous layer is from about 300 to about 4000 Darcies.

5. The cooling product of claim 1, wherein the du Plessis permeability of the first layer is from about 2,500 to about 35,000 Darcies and the du Plessis permeability of the second fibrous layer is from about 500 to about 6000 Darcies.

6. The cooling product of claim 1, wherein the basis weight of the second fibrous layer is less than the basis weight of the first fibrous layer.

7. The cooling product of claim 1, wherein the caliper of the second fibrous layer is less than the caliper of the first fibrous layer.

8. The cooling product of claim 1, wherein the first fibrous layer comprises first synthetic fibers and the second fibrous layer comprises second synthetic fibers, wherein the average denier of the first synthetic fibers is greater than the average denier of the second synthetic fibers.

9. The cooling product of claim 1, wherein the first fibrous layer, the second fibrous layer, or both, comprise a nonwoven web.

10. The cooling product of claim 1, wherein the gelling polymer is a vinyl alcohol polymer.

11. The cooling product of claim 1, wherein gelling polymers constitute from about 30 wt. % to about 90 wt. % of the solids content of the gel.

12. The cooling product of claim 1, wherein gelling polymers constitute from about 40 wt. % to about 70 wt. % of the solids content of the gel.

13. The cooling product of claim 1, wherein the gel further comprises an ionic crosslinking agent.

14. The cooling product of claim 1, wherein the gel further comprises a plasticizer, cooling agent, preservative, or a combination thereof.

15. The cooling product of claim 1, wherein the add-on level of the gel is from about 800% to about 2000%.

16. The cooling product of claim 1, wherein the gel has a moisture content of from about 75 wt. % to about 95 wt. %.

17. The cooling product of claim 1, wherein the gel has a moisture content of from about 80 wt. % to about 90 wt. %.

18. The cooling product of claim 8, wherein the ratio of the average denier of the first synthetic fibers to the average denier of the second synthetic fibers is from about 2.0 to about 10.0.

19. The cooling product of claim 8, wherein the first synthetic fibers comprise a mixture of small denier fibers and large denier fibers.

20. The cooling product of claim 19, wherein the small denier fibers have a denier of from about 2 to about 10 and the large denier fibers have a denier of from about 4 to about 20.

21. The cooling product of claim 9, wherein the nonwoven web is a bonded carded web.

22. The cooling product of claim 10, wherein the vinyl alcohol polymer has a degree of hydrolysis of about 90 mole % or greater.

23. The cooling product of claim 22, wherein the crosslinked network further comprises a vinyl alcohol polymer having a degree of hydrolysis of less than about 90 mole %.

24. The cooling product of claim 13, wherein the ionic crosslinking agent comprises borate ions.

25. The cooling product of claim 14, wherein the cooling agent comprises menthol.

* * * * *